US008212022B2

(12) United States Patent
Micinski et al.

(10) Patent No.: US 8,212,022 B2
(45) Date of Patent: *Jul. 3, 2012

(54) EFFECT OF CARBOHYDRATE CONCENTRATION ON SUCRALOSE EXTRACTION EFFICIENCY

(75) Inventors: Edward Micinski, Martinez, GA (US); James Edwin Wiley, Jr., Daphne, AL (US)

(73) Assignee: Tate & Lyle Technology Limited, London (GB)

( * ) Notice: Subject to any disclaimer, the term of this patent is extended or adjusted under 35 U.S.C. 154(b) by 452 days.

This patent is subject to a terminal disclaimer.

(21) Appl. No.: 12/416,520

(22) Filed: Apr. 1, 2009

(65) Prior Publication Data

US 2010/0081803 A1 Apr. 1, 2010

Related U.S. Application Data

(60) Provisional application No. 61/042,103, filed on Apr. 3, 2008.

(51) Int. Cl.
*C07H 1/06* (2006.01)

(52) U.S. Cl. .................................................. 536/127

(58) Field of Classification Search ................... 536/127
See application file for complete search history.

(56) References Cited

U.S. PATENT DOCUMENTS

| | | | |
|---|---|---|---|
| 4,362,869 A | 12/1982 | Jenner et al. | |
| 4,380,476 A | 4/1983 | Mufti et al. | |
| 4,405,654 A | 9/1983 | Lee | |
| 4,783,526 A | 11/1988 | O'Brien et al. | |
| 4,826,962 A | 5/1989 | Rathbone et al. | |
| 4,889,928 A | 12/1989 | Simpson | |
| 4,950,746 A | 8/1990 | Navia | |
| 4,980,463 A | 12/1990 | Walkup et al. | |
| 5,023,329 A | 6/1991 | Neiditch et al. | |
| 5,034,551 A | 7/1991 | Vernon et al. | |
| 5,089,608 A | 2/1992 | Walkup et al. | |
| 5,128,248 A | 7/1992 | Dordick et al. | |
| 5,141,860 A | 8/1992 | Bornemann et al. | |
| 5,270,071 A | 12/1993 | Sharp et al. | |
| 5,272,137 A | 12/1993 | Blase et al. | |
| 5,298,611 A | 3/1994 | Navia et al. | |
| 5,354,902 A | 10/1994 | Merciadez et al. | |
| 5,374,659 A | 12/1994 | Gowan | |
| 5,384,311 A | 1/1995 | Antenucci et al. | |
| 5,397,588 A | 3/1995 | Antenucci et al. | |
| 5,409,907 A | 4/1995 | Blase et al. | |
| 5,426,220 A | 6/1995 | Baniel | |
| 5,440,026 A | 8/1995 | Khan et al. | |
| 5,470,969 A | 11/1995 | Sankey et al. | |
| 5,498,709 A * | 3/1996 | Navia et al. ................... | 536/124 |
| 5,530,106 A | 6/1996 | Navia et al. | |
| 5,593,696 A | 1/1997 | McNally et al. | |
| 5,621,005 A | 4/1997 | Gowan | |
| 5,658,919 A | 8/1997 | Ratnaraj et al. | |
| 5,674,522 A | 10/1997 | Shah et al. | |
| 5,817,340 A | 10/1998 | Roche et al. | |
| 5,876,759 A | 3/1999 | Gowan | |
| 5,977,349 A | 11/1999 | Catani et al. | |
| 6,080,481 A | 6/2000 | Ochs et al. | |
| 6,090,401 A | 7/2000 | Gowan et al. | |
| 6,176,935 B1 | 1/2001 | Brahmbhatt | |
| 6,211,246 B1 | 4/2001 | Gelotte et al. | |
| 6,258,381 B1 | 7/2001 | Luber et al. | |
| 6,265,012 B1 | 7/2001 | Shamil | |
| 6,277,409 B1 | 8/2001 | Luber et al. | |
| 6,646,121 B2 | 11/2003 | El Kabbani et al. | |
| 6,723,877 B1 | 4/2004 | Maliszewskyj | |
| 6,809,198 B2 | 10/2004 | El Kabbani et al. | |
| 6,890,581 B2 | 5/2005 | Vernon et al. | |
| 6,939,962 B2 | 9/2005 | Clark et al. | |
| 6,943,248 B2 | 9/2005 | Catani et al. | |
| 6,998,144 B2 | 2/2006 | Merkel et al. | |
| 6,998,480 B2 | 2/2006 | Catani et al. | |
| 7,049,435 B2 | 5/2006 | Catani et al. | |
| 2002/0157937 A1 | 10/2002 | Cockrem | |
| 2004/0030124 A1 | 2/2004 | Catani et al. | |
| 2006/0149084 A1 | 7/2006 | Domschke | |
| 2006/0188629 A1 | 8/2006 | Liesen et al. | |
| 2006/0205936 A1 | 9/2006 | Jia et al. | |
| 2006/0276639 A1 | 12/2006 | Fry | |
| 2007/0015916 A1 | 1/2007 | El Kabbani et al. | |

(Continued)

FOREIGN PATENT DOCUMENTS

| | | |
|---|---|---|
| DE | 10260085 | 7/2004 |
| EP | 0043649 | 1/1982 |
| EP | 0409549 | 1/1991 |
| EP | 0708110 | 4/1996 |
| GB | 1426018 | 2/1976 |

(Continued)

OTHER PUBLICATIONS

Bonomelli, Federico & Klein, Didier; "International Search Report"; Dec. 18, 2009; 12 pp; European Patent Office, Rijswijk, The Netherlands.
Grand, Dr. Simon; Combined Search and Examination Report; Dec. 18, 2008; 7 pp; South Wales.
DeSilva, F., Water Quality Products, 2006, 11(4), pp. 1-3.
Ault , A.. Techniques and Experiments for Organic Chemistry, 1987, pp. 43-44.
Chen et al., Ind. Engg. Chem. Res., 1999, 38, 1605-1610.
Grant et al, Chemical Dictionary, 1987, p. 122.
Merck Index, 1996, p. 549.

(Continued)

*Primary Examiner* — Shaojia Anna Jiang
*Assistant Examiner* — Ganapathy Krishnan
(74) *Attorney, Agent, or Firm* — RatnerPrestia (57) ABSTRACT

A process for the purification of aqueous feed streams containing sucralose and/or sucralose 6-esters includes, providing an aqueous feed stream including the sucralose and/or sucralose 6-esters, concentrating the aqueous feed stream to form a concentrated aqueous feed stream containing at least 10 wt % total carbohydrates and extracting the concentrated aqueous feed stream with an organic solvent and producing an organic extract and an aqueous extract, in which the organic solvent is immiscible with water, and in which the carbohydrate preferentially passes into the organic extract.

34 Claims, 6 Drawing Sheets

U.S. PATENT DOCUMENTS

| | | |
|---|---|---|
| 2007/0100139 A1 | 5/2007 | Fry |
| 2007/0160732 A1 | 7/2007 | Deshpande et al. |
| 2007/0227897 A1 | 10/2007 | Li et al. |
| 2007/0270583 A1 | 11/2007 | Ratnam et al. |
| 2008/0227971 A1 | 9/2008 | Leinhos |

FOREIGN PATENT DOCUMENTS

| | | |
|---|---|---|
| WO | 0014052 | 3/2000 |
| WO | 02074403 | 9/2002 |
| WO | WO 03/076453 | 9/2003 |
| WO | WO 03/076453 A1 * | 9/2003 |
| WO | WO 03/076454 | 9/2003 |
| WO | WO 2005/090374 | 9/2005 |
| WO | WO 2005/090376 | 9/2005 |
| WO | WO 2006/061855 | 6/2006 |
| WO | WO 2006/130169 | 12/2006 |
| WO | WO 2007/017899 | 2/2007 |
| WO | WO 2007/023505 | 3/2007 |
| WO | WO 2007/052304 | 5/2007 |
| WO | WO 2008/004246 | 1/2008 |
| WO | 2008091539 | 7/2008 |

OTHER PUBLICATIONS

Qin, Y. et al., "Pervaporation Membranes That Are Highly Selective for Acetic Acid over Water," Ind. Eng. Chem. Res., 2003, 42, 582-595.

Schierbaum, Burkhard, et al.; "Isolation of Carboxylic Acids From Aqueous Solutions by Extraction with Dialkylcarboxylic Amides/Trialkylamines"; Chem. Eng. Technol.; 1999; pp. 37-41; vol. 22; US.

Smith et al, Food Additives Databook, 2003, p. 988.

The Free Dictionary, McGraw-Hill, 2003, pp. 1-2.

* cited by examiner

EFFECT OF CARBOHYDRATE CONCENTRATION ON SUCRALOSE EXTRACTION EFFICIENCY

CROSS REFERENCE TO RELATED APPLICATIONS

This application claims priority benefit of U.S. Provisional Appln. No. 61/042,103, filed Apr. 3, 2008, the entirety of which is incorporated herein by reference.

FIELD OF THE INVENTION

This invention relates to sucralose and to methods for its preparation. In particular, this invention relates to the extraction of sucralose containing aqueous feed streams with an organic solvent.

BACKGROUND OF THE INVENTION

Sucralose (4,1',6'-trichloro-4,1',6'-trideoxygalactosucrose), a high-intensity sweetener that can be used in many food and beverage applications, is a galacto-sucrose having the following molecular structure:

SUCRALOSE

Sucralose is made from sucrose by converting the hydroxyls in the 4, 1', and 6' positions to chloro groups. In this process, the stereochemical configuration at the 4 position is inverted.

In one process for making sucralose from sucrose, sucrose is first converted to a sucrose-6-ester, such as sucrose-6-acetate or sucrose-6-benzoate. The sucrose-6-ester is chlorinated by reaction with a chlorination agent and a tertiary amide, and the resulting reaction mixture heated and then quenched with aqueous alkali. The resulting 4,1',6'-trichloro-4,1',6'-trideoxygalactosucrose ester (sucralose-6-ester) is converted to sucralose, which is subsequently purified and isolated.

This process typically provides a product that contains varying amounts of other chlorinated sugar compounds in addition to sucralose. During removal of these impurities the loss of sucralose should be minimized, and the purification and isolation process should be economical to operate on a large scale. Although advances have been made in the purification of sucralose, there is a continuing need for processes that remove impurities from sucralose, produce sucralose in high purity, minimize the yield loss in the purification process, and are economical to operate on a large scale.

SUMMARY OF THE INVENTION

In one aspect, the invention is a process for the extraction of sucralose and/or a sucralose 6-ester from sucralose and/or sucralose 6-ester containing aqueous feed streams. In one embodiment, the process comprises the steps of:

a) extracting an aqueous feed stream comprising sucralose with a first organic solvent and producing a first organic extract and a first aqueous extract, in which the organic solvent is immiscible with water, and a portion of the sucralose passes into the first organic extract;

b) optionally extracting the first organic extract with an aqueous solvent to produce a second organic extract and a second aqueous extract, in which the sucralose preferentially passes into the second aqueous extract, and in which the second aqueous extract is recycled to step a);

c) concentrating the first aqueous extract to form a concentrated aqueous feed stream; and d) extracting the concentrated aqueous feed stream with a second organic solvent and producing a third organic extract and a third aqueous extract, in which the second organic solvent is immiscible with water, and in which the sucralose preferentially passes into the third organic extract.

In another embodiment, the process comprises the steps of:

a) providing an aqueous feed stream comprising a carbohydrate selected from the group consisting of sucralose 6-esters, and mixtures thereof with sucralose;

b) concentrating the aqueous feed stream to form a concentrated aqueous feed stream; and c) extracting the concentrated aqueous feed stream with an organic solvent and producing an organic extract and an aqueous extract, in which the organic solvent is immiscible with water, and in which the carbohydrate preferentially passes into the organic extract.

In one aspect of the invention, the organic solvent is ethyl acetate. In one aspect of the invention, the aqueous feed stream comprises about 4 wt % to about 8 wt % total carbohydrates. In one aspect of the invention, the concentrated aqueous feed stream comprises at least 10 wt % total carbohydrates. In one aspect of the invention, the concentrated aqueous feed stream comprises about 13 wt % to about 25 wt % total carbohydrates. In one aspect of the invention, the aqueous feed stream comprises sucralose. In other aspects of the invention, the partition coefficient for sucralose between the organic extract and the aqueous extract is at least about 1.0, at least 1.1, or between about 1.1 and about 1.6.

DETAILED DESCRIPTION OF THE INVENTION

Unless the context indicates otherwise, in the specification and claims, the terms organic solvent, first organic solvent, second organic solvent, tetrachloro saccharide, trichloro saccharide, dichloro saccharide, salt, sucralose-6-ester, carbohydrate, and similar terms also include mixtures of such materials. The term saccharide includes monosaccharide, disaccharides, and polysaccharides. Solvent means a liquid that dissolves another material. An aqueous solvent is one in which water is the primary (greater than 50 vol % of the solvents present) or only solvent. Partition coefficient, K, of a carbohydrate between an organic solvent and water is the concentration of the carbohydrate in the organic phase divided by the concentration of the carbohydrate in the aqueous phase when equal volumes of organic solvent and water are used. Two solvents are immiscible if, in any proportion, they do not form a homogeneous phase. Crystallization includes processes in which a solution is rendered saturated or supersaturated with respect to a dissolved component, and the formation of crystals of this component is achieved. The initiation of crystal formation can be spontaneous, or it can require the addition of seed crystals. Crystallization also describes the situation in which a solid or liquid material is dissolved in a solvent to yield a solution which is then rendered saturated or supersaturated so as to obtain crystals. Also, included in the term crystallization are the ancillary processes of washing the crystals with one or more solvents, drying the crystals, and harvesting the final product so obtained. Unless otherwise specified, all percentages are percentages by weight, all temperatures are in degrees Centigrade (degrees Celsius), and all solvent ratios are volume to volume.

A process for the preparation of sucralose from sucrose involves the following steps. First, the hydroxyl in the 6 position of sucrose is blocked with an ester group, such as acetate or benzoate. Then the hydroxyls in the 4,1', and 6' positions of the resulting sucrose 6-ester are converted to chloro groups, with inversion of the stereochemical configuration at the 4 position. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference. Then the ester group in the 6 position of the resulting sucralose-6-ester is removed, and sucralose, the resulting product, purified and isolated. The process, or any of the individual steps thereof, can be either batch or continuous processes.

Preparation of Sucralose Containing Feed Streams

Figure 1:
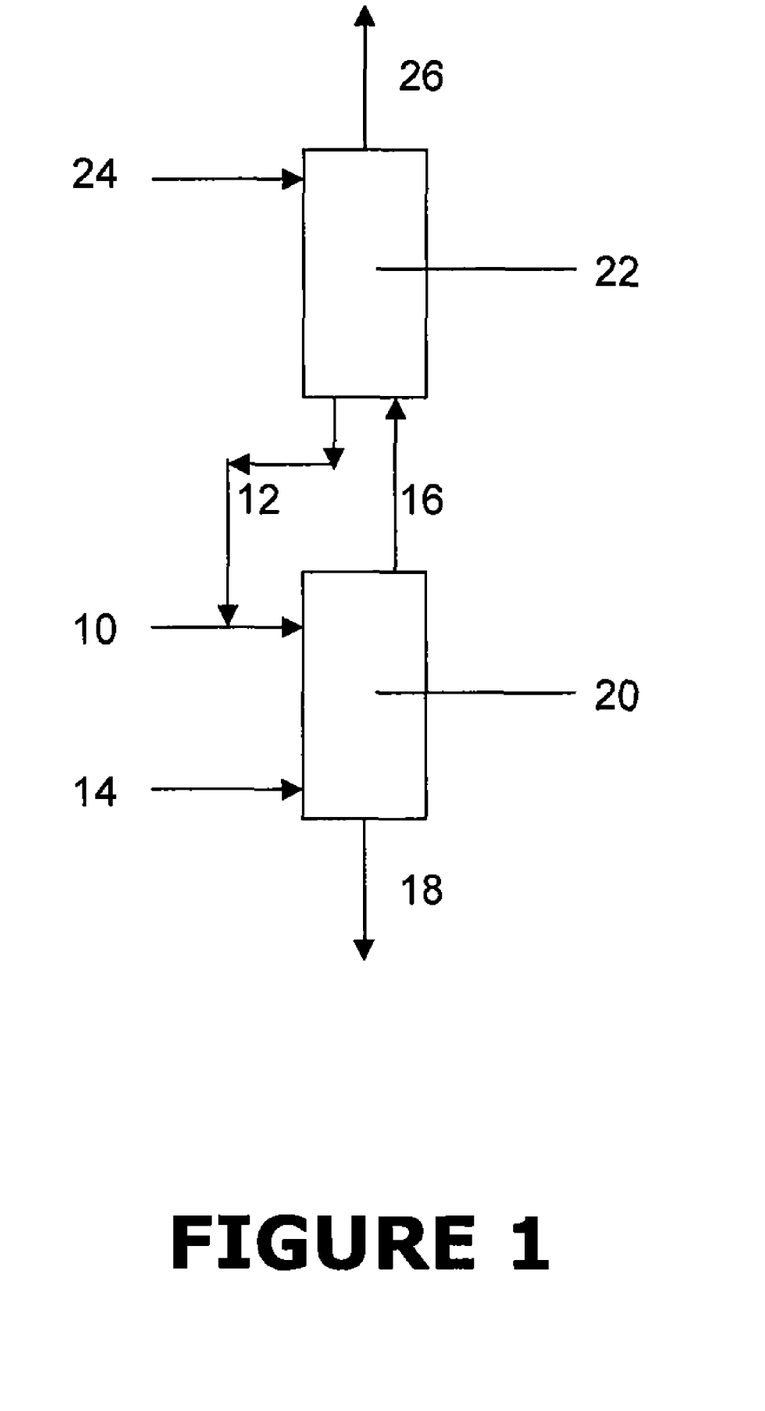
FIG. 1 is flow diagram showing one process for the preparation of an aqueous sucralose containing feed stream.

Referring to FIG. 1, following conversion of sucralose-6-ester to sucralose, an aqueous feed stream (10) that comprises sucralose is produced. Aqueous feed stream 10 typically comprises a total of about of 6 wt % to 50 wt %, for example, about 6 wt % to 12 wt %, about 12 wt % to 18 wt %, about 18 wt % to 25 wt %, or about 25 wt % to about 50 wt % of carbohydrates in a stream in which water is the primary or only solvent. Of the carbohydrates present, between 50% and 80% are typically sucralose. The other carbohydrates primarily fall into one of three categories based on the number of chlorine atoms on the molecule: tetrachloro saccharide impurities (tetrachloro saccharides), dichloro saccharide impurities (dichloro saccharides), and trichloro saccharide impurities (trichloro saccharides). The location and extent of chlorination strongly affects the polarity of the resulting saccharide. In general, the tetrachloro saccharides impurities are less polar than sucralose, and the dichloro saccharide impurities are more polar than sucralose. Generally, more polar impurities are more soluble than sucralose in more polar solvents, and less polar impurities are more soluble than sucralose in less polar solvents.

Other materials that can be present in aqueous feed stream 10 include inorganic salts, such as alkali metal chlorides such as sodium chloride, alkaline earth chlorides, and ammonium chloride; and organic salts, primarily alkali metal acetates, such as sodium acetate; dimethyl amine hydrochloride; and alkali metal formates, such as sodium formate. A small amount, typically less than 5,000 ppm, of the polar aprotic solvent used in the chlorination step, typically N,N-dimethyl formamide, can also be present in the feed stream.

Aqueous feed stream 10 and, optionally, second aqueous extract 12, discussed below, are combined to produce a combined aqueous stream, which is extracted with a stream of a first organic solvent (14) to produce a first organic extract (16) and a first aqueous extract (18). This extraction step is referred to as step EXT1. Because the less polar compounds are preferentially extracted into first organic extract 16, this extraction removes less polar compounds, which include the tetrachloro saccharides, from the combined aqueous stream, as well as a portion of the sucralose from the combined aqueous stream. By "a portion of the sucralose" is meant an amount which, depending upon the embodiment, may be less than 50% or may be more than 50%. The extraction can be carried out under conditions in which greater than 50%, greater than 55%, greater than 60%, or greater than 65%, of the sucralose and 95% of the tetrachloro saccharide impurities in the aqueous feed stream are extracted into first organic extract 16. In an alternative embodiment, the extraction can be carried out as disclosed in WO03/076453, namely wherein a majority (i.e. greater than 50%) of the tetrachlorosucrose compounds in the aqueous feed stream 10 are extracted into the first organic extract 16, and a majority (i.e. greater than 50%) of the sucralose is retained in the first aqueous extract 18.

The choice of solvent is determined by the relative solubilities of sucralose and the principal impurities in the organic solvent and in the aqueous feed stream, as well as such other factors as flammability, ease of recycling within the process, environmental concerns, toxicity, and cost. If desired, the organic solvent can be intentionally saturated with water before use in the extraction step. Mixtures of organic solvents can be used. Solvents contemplated for use as the first organic solvent include those that are immiscible with water and in which halogenated sucrose derivatives, such as sucralose, are readily soluble. Also included are solvents that are partially soluble in a first solvent such as water, an aqueous solution, or other solvent in which halogenated sucrose derivatives are readily soluble, but in which the second solvent still forms a separate phase when mixed with the first solvent in proper ratios and under proper conditions. Typical first organic solvents include, but are not limited to, methyl acetate, ethyl acetate, methyl ethyl ketone, methyl iso-butyl ketone, methyl iso-amyl ketone, methylene chloride, chloroform, diethyl ether, methyl t-butyl ether, n-pentane, n-hexane, n-heptane, n-octane, isooctane, 1,1,1-trichloroethane, n-dodecane, white spirit, turpentine, cyclohexane, propyl acetate, butyl acetate, amyl acetate, carbon tetrachloride, xylene, toluene, benzene, trichloroethylene, 2-butoxyethanol acetate (butyl CELLOSOLVE® acetate), ethylene dichloride, butanol, morpholine, and mixtures thereof. The first organic solvent preferably comprises methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, or n-butanol, either as a single solvent, or as a mixed solvent with these solvents, or with other solvents from the first list. The first solvent more preferably comprises ethyl acetate, iso-propyl acetate, n-propyl acetate, n-butyl acetate, methyl iso-butyl ketone, or n-butanol, either as a single solvent, or as a mixed solvent with these solvents, or with other solvents from the first or second list. Ethyl acetate is the most preferred solvent. Diethyl ether, methyl t-butyl ether, n-pentane, n-hexane, n-heptane, n-octane, isooctane, 1,1,1-trichloroethane, n-dodecane, white spirit, turpentine, cyclohexane, carbon tetrachloride, xylene, toluene, benzene, trichloroethylene, 2-butoxyethanol acetate (butyl CELLOSOLVE® acetate), ethylene dichloride, and morpholine are generally not preferred as single solvents, but may be used in mixed solvents as described.

Extraction is carried out in a first liquid extractor (20), which can be any type of liquid-liquid extractor known in the art, for example, a conventional mixer-settler or a bank of conventional mixer-settlers, an Oldshue-Rushton multiple-mixer column, a sieve tray column, a random packed column, a pulsed packed column, a structured (SMVP) packing column, an asymmetric rotating disk extractor (ARD), a KARR® column, a Kuhni extractor, a Treybel extractor, a Scheibel column, a rotating disc contactor (RDC) column, or a centrifugal extractor such as a Podbielniak centrifugal extractor or a Robatel centrifugal extractor. An extractor with five or more theoretical stages of extraction can be used. A first organic solvent 14, for example ethyl acetate, which if desired can be saturated with water, is fed to the bottom of extractor 20 in proportion to the total amount of feed to the top of extractor 20.

First aqueous extract 18 comprises sucralose as well as some impurities, primarily salts and saccharide impurities that are more polar than sucralose or which have about the same polarity as sucralose. First aqueous extract 18 is used as the feed stream for additional purification steps, described below.

First organic extract 16 can be sent to a second liquid extractor (22) to recover sucralose from first organic extract 16 while leaving the bulk of the less polar impurities in an organic extract. This extraction step is referred to as step EXT1B. If the process comprises additional purification steps, if desired, one or more other recycle streams from these additional purification steps can be recycled to second liquid extractor 22. Second liquid extractor 22 can be any type of liquid-liquid extractor known in the art, examples of which are listed above. An extractor with five or more theoretical stages of extraction can be used. First organic extract 16 is fed into the bottom of liquid extractor 22. A stream (24) of water, which if desired can be saturated with the same organic solvent used in first liquid extractor 20, for example water saturated with ethyl acetate, is fed into the top of extractor 22. The mass ratio of water to first organic extract 16 is typically about 0.8 to about 0.9. An interface between the two phases is maintained in the bottom of second liquid extractor 22 where the aqueous phase, second aqueous extract 12, is collected. Second aqueous extract 12 can be recycled to first liquid extractor 20. Greater than 85%, 90%, 92%, or 95% of the sucralose present in the first organic phase is extracted into the second aqueous phase by step EXT1B.

The organic extract, second organic extract 26, exits the top of extractor 22. Second organic extract 26 contains less polar impurities, such as the tetrachloro saccharides. It is purged from the process, and the organic solvent recovered for reuse.

Figure 2:
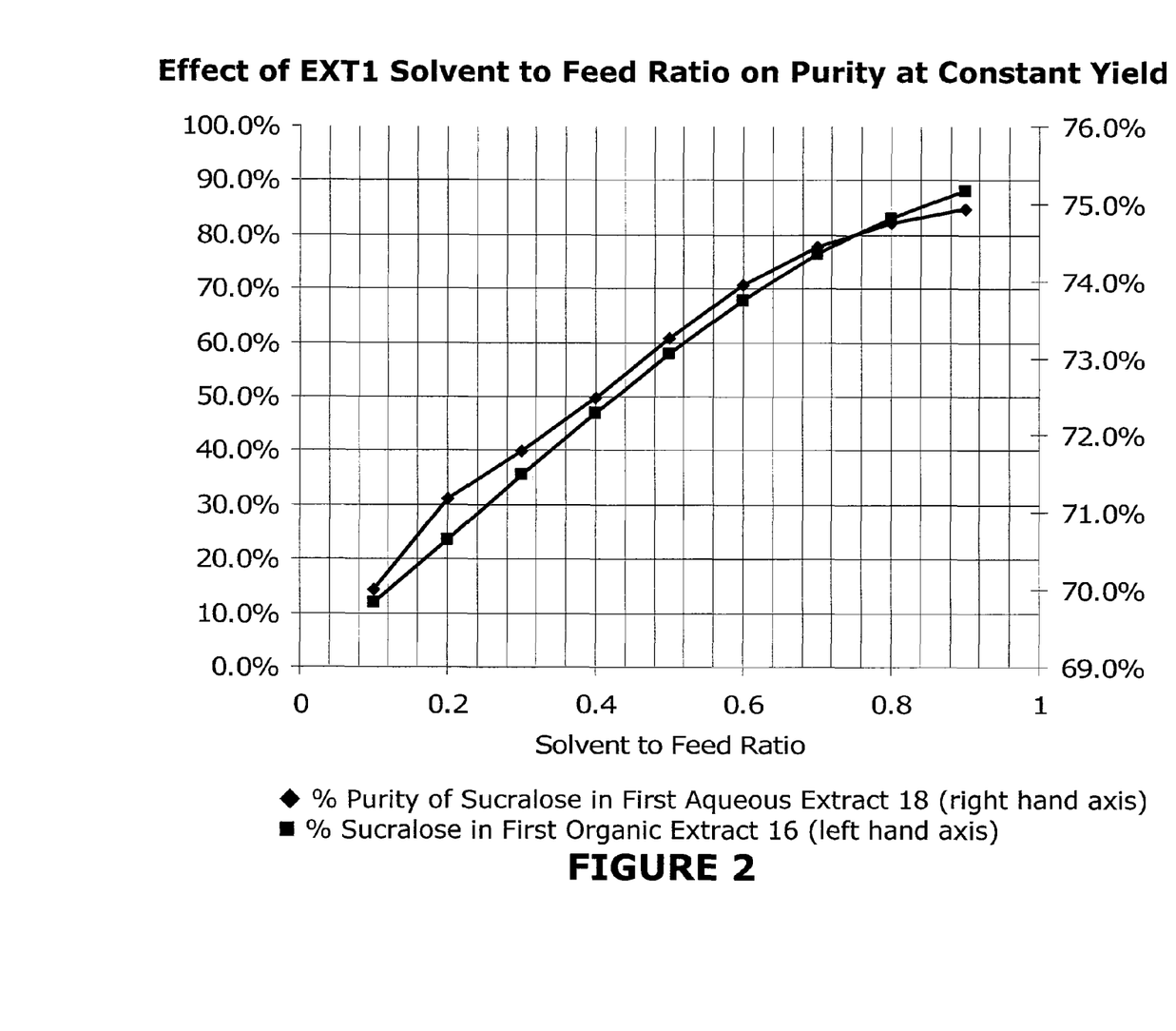
FIG. 2 shows the effect of the ratio of organic solvent ("solvent") to aqueous sucralose containing feed stream ("feed") at constant sucralose yield on the purity of the sucralose in the first aqueous extract.

In one aspect of the invention, the mass ratio of first organic solvent 14 to the combined aqueous feed stream in the first extraction step (EXT1) is about 0.4 to about 0.9. Preferably, the mass ratio of first organic solvent 14 to aqueous feed stream 10 in step EXT1 is about 0.6 to about 0.9. FIG. 2 shows the amount of sucralose in first organic extract 16 (left hand axis) and the purity of the sucralose in first aqueous extract 18 (right hand axis) as a function of the ratio of first organic solvent 14 to combined aqueous feed stream in the first extraction step (EXT1), calculated at constant sucralose yield. These values are for the process described above, a process in which a sucralose containing aqueous feed stream is extracted with an organic solvent in a first extraction step, the resulting organic extract is back extracted with water in a second extraction step, and the resulting second aqueous extract is recycled to the first extraction step.

As can be seen from FIG. 2, when mass ratio of organic solvent 14 to combined aqueous feed stream in the first extraction step is about 0.4 or greater, about 50% or more of the sucralose is extracted into first organic extract 16. When the mass ratio is 0.5 or greater, greater than about 60% of the sucralose is extracted into first organic extract 16. When the mass ratio is 0.6 or greater, greater than about 65% of the sucralose is extracted into first organic extract 16. Surprisingly, the level of impurities in first aqueous extract 18 is reduced significantly, with little or no decrease in overall sucralose yield, when higher organic solvent to the combined aqueous feed stream ratios are used in the first extraction step.

Purification of Sucralose Containing Feed Streams

Figure 3:
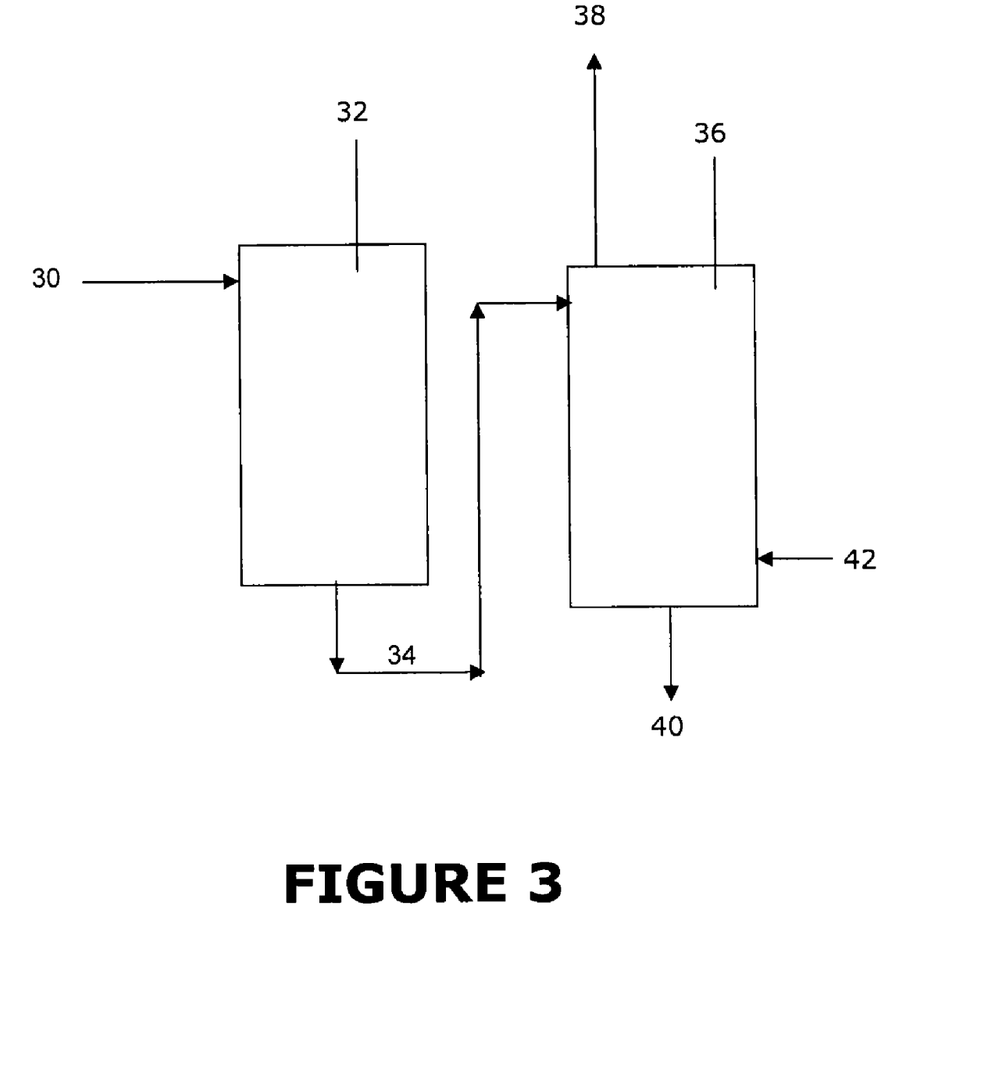
FIG. 3 is flow diagram showing a process of the invention.
Figure 4:
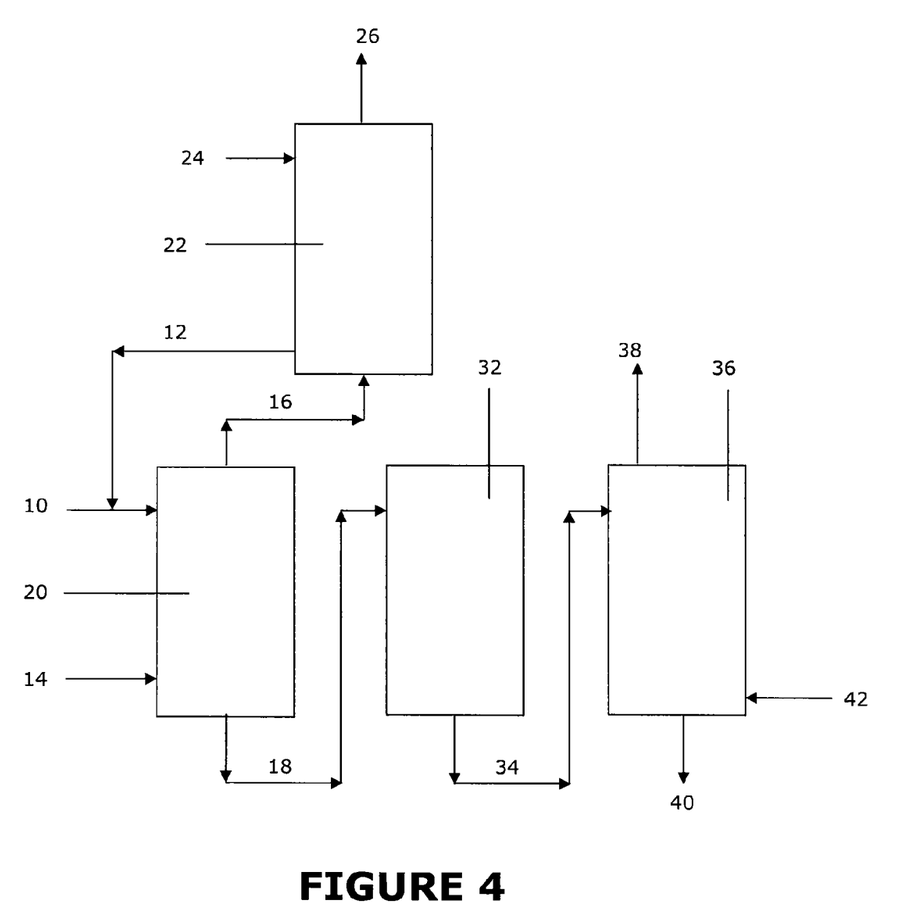
FIG. 4 is flow diagram showing a process of the invention in which there are multiple extraction steps.

Referring to FIG. 3, feed stream 30 is fed into a concentrator (32). Concentrator 32 can be designed for either batch or continuous operation. Concentrator 32 can be any type of evaporator known in the art, for example, a falling film evaporator, a thin-film evaporator, a wiped film evaporator, a forced circulation evaporator, a bulk evaporator, a Robert evaporator, a Herbert evaporator, a Caddie-type evaporator, or an Oskar evaporator. The sucralose containing aqueous feed stream 30 can be, for example, sucralose containing aqueous feed stream 10 produced by hydrolysis of sucralose-6-ester to sucralose. Alternatively, the feed stream can have undergone processing to remove some of the impurities. For example, aqueous feed streams that have been processed to remove less polar impurities, such as first aqueous extract 18, can be used as the feed stream to the process. FIG. 4 shows a process in which the sucralose containing aqueous feed stream is first aqueous extract 18. Other sucralose containing aqueous feed stream can be used in the process of the invention. If a multi-step process is used for the purification and isolation of sucralose, sucralose containing aqueous feed stream from other steps later in the process can also be fed to concentrator 32.

Concentrator 32 increases the concentrations of carbohydrates, including the concentration of sucralose, and, if present, the salt present in sucralose containing aqueous feed stream 30. Concentrator 32 typically increases the concentration of carbohydrates in sucralose containing aqueous feed stream 30 by a factor of about 1.1 to about 4, or about 1.15 to about 2.5, or about 1.2 to about 2.0. Sucralose containing aqueous feed stream 30 entering concentrator 32 can have less than about 10 wt %, less than 9 wt %, or less than 8 wt % total carbohydrates, for example, about 3 wt % to about 9 wt % or to about 10 wt %; about 4 wt % to about 8 wt %; about 5 wt % to about 7 wt %; or about 6 wt % to about 7 wt % of total carbohydrate. Sucralose containing aqueous feed stream 30 can contain up to 18 wt % of inorganic salts, primarily alkali metal chlorides, such as sodium chloride, and/or ammonium chloride, and organic salts, primarily alkali metal acetates, such as sodium acetate. Concentrated sucralose containing aqueous feed stream 34 leaving concentrator 32 can have at least about 10 wt %, at least about 12 wt %, or at least about 13 wt % total carbohydrate; for example, about 10 wt %, about 12 wt %, about 15 wt %, or about 18 wt % to about 25 wt %; about 10 wt %, about 12 wt %, about 15 wt %, or about 18 wt % to about 20 wt %; about 10 wt %, about 12 wt %, or about 15 wt % to about 18 wt %; about 13 wt % to about 17 wt %; about 14 wt % to about 16 wt %; or about 15 wt % to about 16 wt % total carbohydrate. Typically, sucralose comprises about 60% to 80% of the carbohydrates present in concentrated sucralose containing aqueous feed stream 34.

Concentrated aqueous stream 34 is fed to third liquid extractor 36. This extraction step is referred to as step EXT2. In this extraction step, sucralose is extracted into a stream of a second organic solvent (42) to form the third organic extract (38). Most of the more polar impurities and most of the salts present remain in the third aqueous extract (40). Third aqueous extract 40 exits the bottom of third liquid extractor 36 and is purged from the process. Alternatively, third aqueous extract 40 can be back extracted with an organic solvent, such as ethyl acetate, before being purged from the process. The recycle stream from this back extraction of third aqueous extract 40 can be combined with the solvent feed to extractor 36 (stream 42) or, if the process comprises additional extractions steps prior to the concentration step, the recycle stream can be fed, for example, to second liquid extractor 22.

Figure 5:
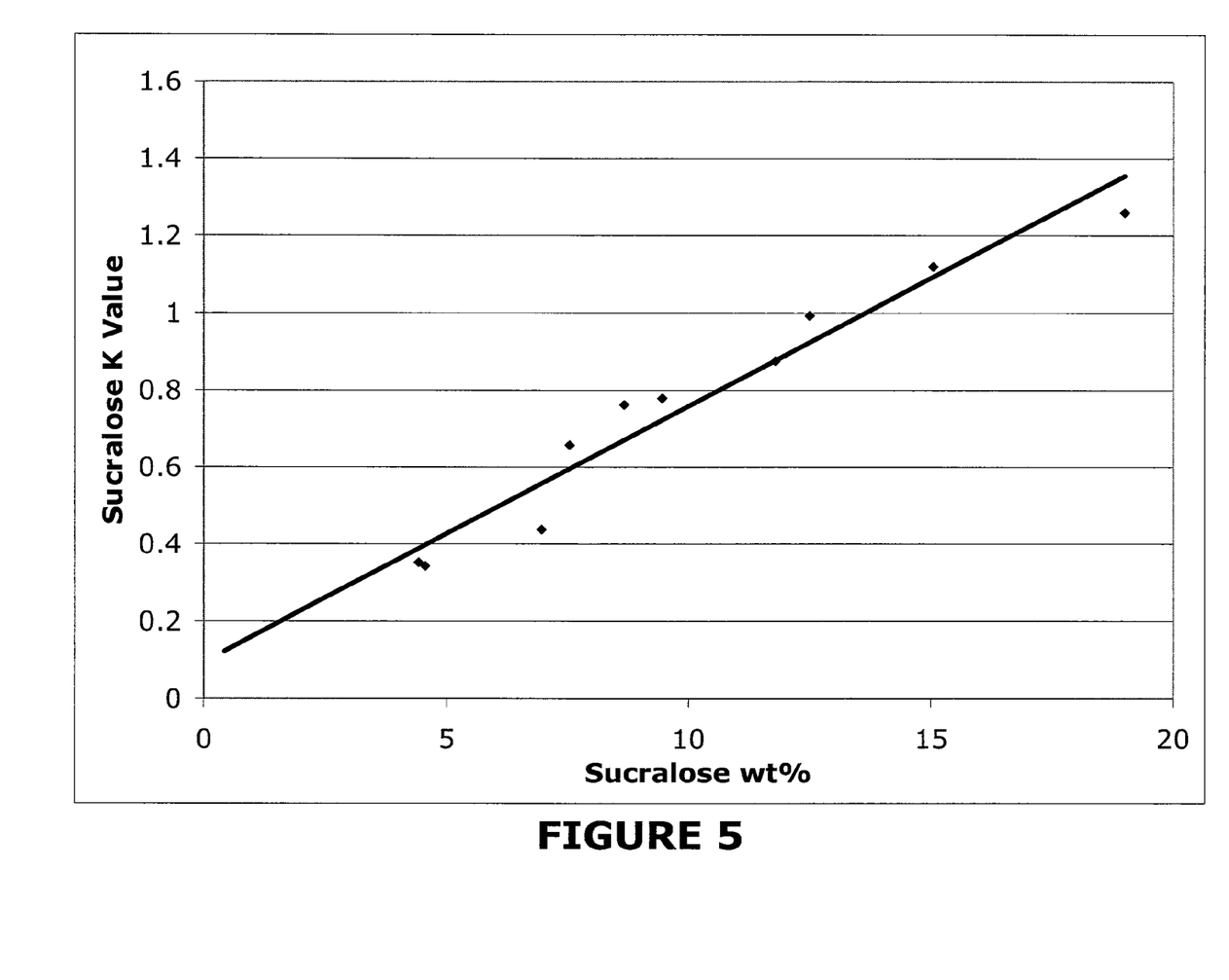
FIG. 5 is a plot showing the effect of sucralose concentration on the partition coefficient, K, of sucralose between an organic solvent and water.
Figure 6:
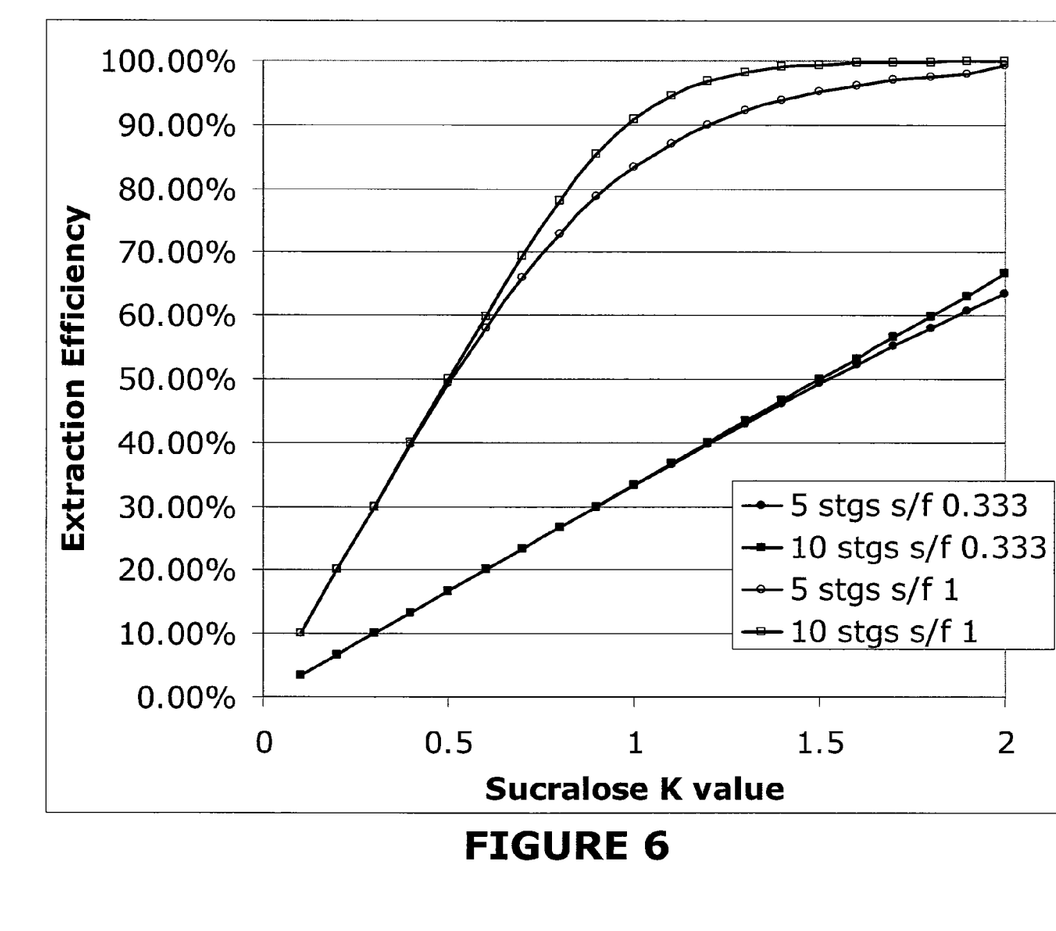
FIG. 6 is a plot showing the effect of the ratio of organic solvent to sucralose containing feed stream in extraction EXT2 on the yield of sucralose.

Surprisingly, K, the partition coefficient for sucralose between an organic solvent and water when equal volumes of organic solvent and water are used is dependent on the concentration of carbohydrates. As shown in FIG. 5, when equal volumes of ethyl acetate and water are used, K increases from 0.4, when the initial concentration of sucralose in the aqueous phase is about 5 wt % to about 1.1 when the initial concentration of sucralose in the aqueous phase is about 15 wt % and about 1.2 when the initial concentration of sucralose in the aqueous phase is about 16 wt %. As shown in FIG. 6, when the ratio of organic solvent to water is 1, the extraction efficiency increases from about 40% to about 90% when the K value increases from about 0.4 to about 1.1 and the extraction efficiency increases from about 40% to over 90% when the K value increases from about 0.4 to about 1.2. Therefore, before the sucralose is extracted into an organic solvent, it is advantageous that sucralose containing aqueous feed stream 18 be concentrated before extraction with the organic solvent. Preferably, the extraction can be carried out under conditions at which the partition coefficient for sucralose between the organic extract and the aqueous extract is at least about 1.0, more preferably at least about 1.1 or at least about 1.2. The partition coefficient is typically in the range of about 1.0 to about 1.6, about 1.1 to about 1.6, about 1.2 to about 1.6, or about 1.25 to 1.6.

Alternatively, the feed stream to concentrator 32 can comprise a sucralose-6-ester, such as sucralose-6-acetate or sucralose-6-benzoate, in addition to, or in place of sucralose, at concentrations the same as those for sucralose, given above. Concentrator 32 typically increases the concentration of carbohydrates in sucralose containing aqueous feed stream 30 by a factor of about 1.1 to about 4, or about 1.15 to about 2.5, or about 1.2 to about 2.0. Concentration of a feed stream comprising a sucralose-6-ester in the manner described above also increases the extraction efficiency of the ester into the organic solvent. The partition coefficient for a sucralose-6-ester, such as sucralose-6-acetate, between an organic solvent, such as ethyl acetate, and water when equal volumes of organic solvent and water are used is larger that the corresponding value for sucralose measured under the same conditions.

The extraction step (EXT2) can be either batch or continuous. Third liquid extractor 36 can be any type of liquid-liquid extractor known in the art, examples of which are given above. Concentrated aqueous stream 34 is fed to the top of third liquid extractor 36 and a stream of second organic solvent 42, is fed to the bottom of extractor 36. The ratio (volume to volume) of second organic solvent 42 to aqueous feed stream 34 is in the range of about 1.5 to about 4.0, for example, about 1.5 to about 2.0, or about 2.0 to about 2.5, or about 2.5 to about 4.0. However, if the number of theoretical stages of extraction in third liquid extractor 36 is increased, the volume of second organic solvent 42, and consequently the ratio of second organic solvent 42 to aqueous feed stream 34, could be reduced.

Any of the organic solvents used as the first organic solvent can be used as the second organic solvent. However, as a result of this extraction step, sucralose is transferred from an aqueous extract to an organic extract, so, if sucralose is to be crystallized from the organic solvent, it is convenient to use a second organic solvent that can be used as the crystallization solvent for sucralose. It is also convenient for the first organic solvent and the second organic solvent to be the same organic solvent. A preferred second organic solvent is ethyl acetate.

The process of the invention can be combined with the process for the removal of non-polar materials from aqueous sucralose containing process streams described above. In this process, second aqueous extract 18 is fed to concentrator 32. The combined process is shown in FIG. 4. Feed streams that comprise sucralose and/or sucralose-6-esters can be purified by the combined process.

Preparation of Sucrose-6-Ester

Selective protection of the 6-hydroxyl of sucrose can be carried out by reaction of sucrose with a carboxylic acid anhydride, such as acetic anhydride or benzoic anhydride, in an anhydrous polar aprotic solvent in the presence of an organotin-based acylation promoter, at a temperature and for a period of time sufficient to produce the sucrose-6-ester. The 6-ester group shields the hydroxyl on the 6 position from the chlorination reaction. Accordingly, any ester group that is stable to the conditions of the chlorination reaction and that can be removed under conditions that do not affect the resulting sucralose can be used. When sucrose-6-acetate is prepared, 1,3-diacetoxy-1,1,3,3-tetrabutyldistannoxane, for example, can be used as the organotin-based acylation promoter and acetic anhydride as the carboxylic acid anhydride. Preparation of sucrose-6-esters is disclosed in, for example, O'Brien, U.S. Pat. No. 4,783,526; Navia, U.S. Pat. No. 4,950,746; Simpson, U.S. Pat. No. 4,889,928; Neiditch, U.S. Pat. No. 5,023,329; Walkup, U.S. Pat. No. 5,089,608; Vernon, U.S. Pat. No. 5,034,551; Sankey, U.S. Pat. No. 5,470,969; Kahn, U.S. Pat. No. 5,440,026; Clark, U.S. Pat. No. 6,939,962, and Li, U.S. Pat. Pub. 2007/0227897 A1; the disclosures of which are all incorporated herein by reference.

Preparation of Sucralose-6-Ester Containing Feed Streams

To convert sucrose-6-ester to sucralose-6-ester, the hydroxyls at the 4, 1', and 6' positions of the sucrose-6-ester are converted to chloro groups, and the stereochemical configuration at the 4 position is inverted. Conversion of the hydroxyls in the 4, 1', and 6' positions of the ester to chloro groups with inversion of the stereochemical configuration at the 4 position is disclosed in Walkup, U.S. Pat. No. 4,980,463; Jai, U.S. Pat. Pub. 2006/0205936 A1; and Fry, U.S. Pat. Pub. 2007/0100139 A1; the disclosures of which are all incorporated herein by reference.

The chlorination process comprises the following steps. A reaction mixture is prepared comprising the sucrose-6-ester, a tertiary amide, and at least seven molar equivalents of a chlorination agent. For example, in one process, the sucrose-6-ester can be added in a feed stream that comprises about 20 wt % to about 40 wt % of the sucrose-6-ester. The ratio by weight of tertiary amide to total carbohydrate in the reaction mixture may be about 5:1 to about 12:1. Alternatively, a preformed chloroformiminium salt, such as (chloromethylene)dimethylammonium chloride (Arnold's reagent), can be used. (Chloromethylene)dimethylammonium chloride can be prepared, for example, by the reaction of phosgene with N,N-dimethyl formamide. Typically, the molar ratio of the (chloromethylene)dimethylammonium salt to the sucrose-6-ester is about 7:1 to about 11:1.

Subsequently, the hydroxyl groups of the sucrose-6-ester at the 2, 3, 4, 1', 3', 4', and 6' positions are converted to O-alkylformiminium groups. The resulting reaction mixture is heated at a temperature or temperatures and for a period of time or times sufficient to produce a product containing a derivative of sucralose-6-ester in which the remaining hydroxyl groups remain as O-alkylformiminium groups. For example, Walkup, U.S. Pat. No. 4,980,463, the disclosure of which is incorporated herein by reference, and Fry, U.S. 2007/0100139, the disclosure of which is incorporated herein by reference, disclose such processes.

Because formation of a chloroformiminium salt or Vilsmeier reagent is not essential to the chlorination reaction, chlorination agent refers to any compound that can be used to form a chloroformiminium salt or Vilsmeier reagent, or that can convert the hydroxyl groups of a sucrose-6-ester to chloro groups. Some chlorination agents that can be reacted with a tertiary amide to form a chloroformiminium salt include, for example, phosgene, phosphorus oxychloride, phosphorus pentachloride, thionyl chloride, sulfuryl chloride, oxalyl chloride, trichloromethyl chloroformate ("diphosgene"), bis(trichloromethyl) carbonate ("triphosgene"), and methane sulfonylchloride. Tertiary amides that can be used include, for example, N,N-dimethyl formamide (DMF), N-formyl piperidine, N-formyl morpholine, and N,N-diethyl formamide. When N,N-dimethyl formamide is used as the tertiary amide, it can also be used as the reaction solvent. Co-solvents can be used at up to about 80 vol % or more of the liquid phase of the reaction medium. Useful co-solvents are those which are both chemically inert and which provide sufficient solvent power to enable the reaction to become essentially homogeneous at the monochlorination stage, for example toluene, o-xylene, 1,1,2-trichloroethane, 1,2-diethoxyethane, diethylene glycol dimethyl ether.

Quenching of the reaction mixture restores the hydroxyl groups at the 2, 3, 3', and 4' positions and forms the sucralose-6-ester. The reaction mixture can be quenched by the addition of about 0.5 to about 2.0 molar equivalents, typically about 1.0 to about 1.5 molar equivalents, of alkali relative to the amount of chlorination agent used in the reaction. An aqueous solution of an alkali metal hydroxide, such as sodium or potassium hydroxide; an aqueous slurry of an alkaline earth metal hydroxide, such as calcium hydroxide; or aqueous ammonium hydroxide can be used to quench the reaction. For example, an aqueous solution of an alkali metal hydroxide, such as aqueous sodium hydroxide, that contains about 5 wt % to about 35 wt %, typically about 8 wt % to about 20 wt %, and preferably about 10 wt % to about 12 wt % can be used.

As described below, quenching can be carried out by addition of alkali to the reaction mixture, by the dual stream process, or by the circulated process. In each case pH and temperature are controlled during addition of the alkali. Quenching is typically carried out at a pH between about 8.5 to about 10.5 and at a temperature of about 0° C. to about 60° C. Preferably, the pH should not be permitted to rise above about 10.5 during the course of the quenching reaction.

In the dual stream process, quenching is carried out by slow addition of the aqueous alkali with simultaneous slow addition of the chlorination reaction material into a reaction vessel. The chlorination reaction mixture and aqueous alkali are simultaneously added slowly until the desired quantity of chlorination reaction mixture has been added. Further aqueous alkali is added until the desired pH is reached. Then the temperature and pH are maintained at the desired levels for the remainder of the reaction. This process can be a batch or continuous process.

In the circulated process, quenching is carried out by circulating the chlorination reaction mixture from a vessel through a circulation loop. Chlorination reaction mixture and aqueous alkali are added slowly into this circulation loop. Sufficient aqueous alkali is added until the desired pH is reached. Then the temperature and pH are maintained at the desired levels for the remainder of the reaction. This process can be a batch or continuous process.

Following quenching, the reaction mixture can be neutralized by the addition of aqueous acid, for example aqueous hydrochloric acid. The resulting mixture comprises sucralose 6-ester, other carbohydrate including chlorinated carbohydrate impurities, unreacted tertiary amide, and salts in an aqueous solvent in which the predominant solvent is water.

This sucralose-6-ester containing feed stream can be used as a process in which the sucralose is purified at the sucralose-6-ester stage. In one aspect of the invention, the sucralose-6-ester containing feed stream is concentrated and extracted with an organic solvent as described above. After extraction, if desired, the resulting sucralose-6-ester containing organic extract can be further purified. The sucralose 6-ester is deacylated to sucralose, and the sucralose crystallized. Because the sucralose 6-ester is less polar than sucralose, the partition coefficients for the sucralose 6-ester between an organic solvent and water are much higher than the partition coefficients for the sucralose between an organic solvent and water. Consequently, the sucralose 6-ester is efficiently extracted into the organic solvent rather than remaining in the aqueous solution. Alternatively, the sucralose 6-ester containing aqueous feed stream can be used in a process, described below, in which the sucralose 6-ester is converted to sucralose before purification.

Conversion of Sucralose-6-Ester to Sucralose

The sucralose 6-ester containing aqueous feed stream typically comprises both sucralose and sucralose-6-ester. Methods for hydrolyzing sucralose-6-ester are disclosed, for example in Catani, U.S. Pat. Nos. 5,977,349, 6,943,248, 6,998,480, and 7,049,435; Vernon, U.S. Pat. No. 6,890,581; El Kabbani, U.S. Pat. Nos. 6,809,198, and 6,646,121; Navia, U.S. Pat. Nos. 5,298,611 and 5,498,709, and U.S. Pat. Pub. 2004/0030124; Liesen, U.S. Pat. Pub. 2006/0188629 A1; Fry, U.S. Pat. Pub. 2006/0276639 A1; El Kabbani, U.S. Pat. Pub. 2007/0015916 A1; Deshpande, U.S. Pat. Pub. 2007/0160732 A1; and Ratnam, U.S. Pat. Pub. 2007/0270583 A1; the disclosures of which are all incorporated herein by reference.

For example, (a) sucralose-6-ester can be hydrolyzed to sucralose by raising the pH of the reaction mixture to about 11±1 at a temperature and for a time sufficient to effect removal of the protecting group, and (b) the tertiary amide is removed by, for example, stream stripping. Either step (a) or step (b) can be carried first. Alternatively, conversion of sucralose-6-ester to sucralose can be carried in methanol containing sodium methoxide. A trans-esterification reaction occurs that forms sucralose and the methyl ester of the acid, for example methyl acetate when the sucralose-6-ester is sucralose-6-acetate. The methyl ester of the acid can be removed by distillation, and the resulting sucralose containing product dissolved in water.

INDUSTRIAL APPLICABILITY

The process of the invention is useful in the preparation of sucralose. Sucralose is a high-intensity sweetener that can be used in many food and beverage applications, as well as in other applications. Such applications include, for example, beverages, combination sweeteners, consumer products, sweetener products, tablet cores (Luber, U.S. Pat. No. 6,277, 409), pharmaceutical compositions (Luber, U.S. Pat. No. 6,258,381; Roche, U.S. Pat. No. 5,817,340; and McNally, U.S. Pat. No. 5,593,696), rapidly absorbed liquid compositions (Gelotte, U.S. Pat. No. 6,211,246), stable foam compositions (Gowan, Jr., U.S. Pat. No. 6,090,401), dental floss (Ochs, U.S. Pat. No. 6,080,481), rapidly disintegrating pharmaceutical dosage forms (Gowan, Jr., U.S. Pat. No. 5,876, 759), beverage concentrates for medicinal purposes (Shah, U.S. Pat. No. 5,674,522), aqueous pharmaceutical suspensions (Ratnaraj, U.S. Pat. No. 5,658,919; Gowan, Jr. U.S. Pat. Nos. 5,621,005 and 5,374,659; and Blase, U.S. Pat. Nos. 5,409,907 and 5,272,137), fruit spreads (Antenucci, U.S. Pat. No. 5,397,588; and Sharp, 5,270,071), liquid concentrate compositions (Antenucci, U.S. Pat. No. 5,384,311), and stabilized sorbic acid solutions (Merciadez, U.S. Pat. No. 5,354, 902). The determination of an acceptable sweetness can be accomplished by a variety of standard "taste test" protocols known in the art which are well known to those skilled in the art, such as, for example, the protocols referred to in Merkel, U.S. Pat. No. 6,998,144, and Shamil, U.S. Pat. No. 6,265,012.

The advantageous properties of this invention can be observed by reference to the following examples which illustrate but do not limit the invention.

EXAMPLES

Example 1

This example was generated using a mathematical model that included both a first extraction process (EXT1), a back extraction (EXT1B) of the first organic extract (16), and recycle of the second aqueous extract (12) to the first extraction process. The calculations used in the model were derived from theoretical equations fitted to actual pilot plant data. FIG. 1 shows a flow diagram of the modeled process.

FIG. 2 shows the results from multiple model runs in which the mass ratio of first organic solvent 14 to the combined aqueous feed stream in the first extraction was varied. The number of separation stages in the back extraction was adjusted to maintain an equivalent overall extraction yield. The amount of sucralose extracted into the first organic extract 16 during the first extraction step is shown on the left hand axis. The purity of the sucralose produced by the process is shown on the right hand axis.

As can be seen from FIG. 2, when the mass ratio of organic solvent 14 to combined aqueous feed stream in the first extraction step is about 0.4 or greater, about 50% or more of the sucralose is extracted into first organic extract 16. When the mass ratio is 0.6 or greater, greater than about 65% of the sucralose is extracted into first organic extract 16. Surprisingly, the level of impurities in first aqueous extract 18 is reduced significantly, with little or no reduction in overall sucralose yield, when higher organic solvent to the combined aqueous feed stream ratios are used in the first extraction step.

As can also be seen from FIG. 2, product purity begins to level out near 75%, when nearly 90% of the sucralose is extracted into first organic extract 16.

Example 2

This example shows the effect of sucralose concentration on the partition coefficient of sucralose between an organic phase and aqueous phase. Aqueous solutions of sucralose were prepared at various carbohydrate concentrations. An equal volume of ethyl acetate was then added to each solution and the two phases mixed thoroughly. After the two phases separated, the carbohydrate concentration in each phase was determined. The K value was calculated by dividing the concentration of sucralose in the ethyl acetate phase by the concentration of sucralose in the aqueous phase. FIG. 3 shows the effect of carbohydrate concentration on the partition coefficient, K. The larger the K value, the more readily sucralose is extracted into the ethyl acetate phase.

Example 3

This example measures the effect of concentration on sucralose yield. Two different organic solvent to sucralose containing aqueous feed stream ratios were used: about 3.7:1 and about 3.0:1 (volume to volume). The organic solvent was ethyl acetate. The results are shown in Table 1. In Table 1, "Solvent:Feed" is the ratio (volume to volume) of the organic solvent to the sucralose containing aqueous feed stream. "Carbohydrates" is the wt % of carbohydrates in the sucralose containing aqueous feed stream. "Salt" is the wt % of salt in the sucralose containing aqueous feed stream. "Yield" is the percent of sucralose recovered from the organic phase of the extraction. Because multi-stage contacting devices were used for this testing, K values could not be determined directly from this data and compared to the values determined in Example 2.

TABLE 1

| Concentration | Solvent:Feed | Sucralose (wt %) | Salt (wt %) | Yield (%) |
| --- | --- | --- | --- | --- |
| Low | 3.68 | 6.97 | 8.37 | 97.54 |
| Low | 2.95 | 6.17 | 7.78 | 97.31 |
| High | 3.69 | 13.77 | 15.00 | 99.99 |
| High | 3.91 | 14.46 | 15.13 | 99.94 |
| High | 3.76 | 14.69 | 14.98 | 99.98 |
| High | 3.18 | 13.82 | 14.95 | 100 |

These experiments show a dramatic increase in extraction efficiency when the sucralose containing aqueous feed stream is more concentrated. These extraction efficiencies were inserted into a mathematical model of a purification process for sucralose. Increasing the EXT2 extraction efficiency from 97.5% to 99.5% improves the overall yield of sucralose by >5.5%, when using the same solvent to feed ratio and number of extraction stages.

The disclosure of the invention includes the following claims. Having described the invention, we now claim the following and their equivalents.

What is claimed is:

1. A process comprising the steps of:
   a) extracting an aqueous feed stream comprising carbohydrates, said carbohydrates comprising sucralose, with a first organic solvent and producing a first organic extract and a first aqueous extract, in which the first organic solvent is immiscible with water, and a portion of the sucralose passes into the first organic extract;
b) optionally extracting the first organic extract with an aqueous solvent to produce a second organic extract and a second aqueous extract, in which the sucralose preferentially passes into the second aqueous extract, and in which the second aqueous extract is recycled to step a);
c) concentrating the first aqueous extract to form a concentrated aqueous feed stream comprising at least 10 wt % total carbohydrates; and
d) extracting the concentrated aqueous feed stream with a second organic solvent and producing a third organic extract and a third aqueous extract, in which the second organic solvent is immiscible with water, and in which the sucralose preferentially passes into the third organic extract.

2. The process according to claim 1, wherein step b) is carried out.

3. The process of claim 1 in which the first organic solvent and the second organic solvent are the same organic solvent.

4. The process of claim 1 in which the first organic solvent comprises a solvent selected from the group consisting of methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, n-butanol, and mixtures thereof.

5. The process of claim 1 in which the second organic solvent comprises a solvent selected from the group consisting of methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, n-butanol, and mixtures thereof.

6. The process of claim 1 in which, in step c) the concentration of the carbohydrate in the aqueous feed stream is increased by a factor of about 1.1 to about 4.

7. The process of claim 1 in which, in step d), the partition coefficient for sucralose between the organic extract and the aqueous extract is at least 1.0.

8. The process of claim 1 in which the aqueous feed stream that is extracted in step a) comprises less than about 10 wt % total carbohydrates.

9. The process of claim 1 in which the aqueous feed stream comprises about 3 wt % to about 10 wt % total carbohydrates.

10. The process of claim 1 in which the concentrated aqueous feed stream comprises at least 12 wt % total carbohydrates.

11. The process of claim 1 in which the concentrated aqueous feed stream comprises about 10 wt % to about 25 wt % total carbohydrates.

12. The process of claim 1 in which the concentrated aqueous feed stream comprises about 12 wt % to about 20 wt % total carbohydrates.

13. The process of claim 1 in which the concentrated aqueous feed stream comprises about 12 wt % to about 18 wt % total carbohydrates.

14. The process of claim 1 in which the concentrated aqueous feed stream comprises about 18 wt % to about 25 wt % total carbohydrates.

15. The process of claim 1 in which the concentrated aqueous feed stream comprises about 13 wt % to about 17 wt % total carbohydrates.

16. The process of claim 1 in which, in step a), the mass ratio of the first organic solvent to the aqueous feed stream is about 0.4 to about 0.9.

17. The process of claim 1 in which the chlorinated impurities comprises tetrachloro saccharides, in step a) greater than 50% of the sucralose and at least 95% of the tetrachloro saccharides in the aqueous feed stream pass into the first organic extract, and in step b) greater than 90% of the sucralose in the first organic extract passes into the second aqueous extract, and the tetrachloro saccharides are preferentially retained in the second organic extract.

18. The process of claim 1 in which, in step a), greater than 55% of the sucralose in the aqueous stream passes into the first organic extract.

19. The process of claim 1 additionally comprising the step or steps of purifying and isolating the sucralose.

20. A process comprising the steps of:
a) providing an aqueous feed stream comprising a carbohydrate selected from the group consisting of sucralose 6-esters, and mixtures thereof with sucralose;
b) concentrating the aqueous feed stream to form a concentrated aqueous feed stream comprising at least 10 wt % total carbohydrates; and
c) extracting the concentrated aqueous feed stream with an organic solvent and producing an organic extract and an aqueous extract, in which the organic solvent is immiscible with water, and in which the carbohydrate preferentially passes into the organic extract.

21. The process of claim 20 in which, in step b) the concentration of the carbohydrate the aqueous feed stream is increased by a factor of about 1.1 to about 4.

22. The process of claim 20 in which the carbohydrate is sucralose 6-acetate.

23. The process of claim 20 in which the aqueous feed stream provided in step a) comprises less than 10 wt % total carbohydrates.

24. The process of claim 20 in which the aqueous feed stream comprises about 3 wt % to about 10 wt % total carbohydrates.

25. The process of claim 20 in which the concentrated aqueous feed stream comprises at least 12 wt % total carbohydrates.

26. The process of claim 20 in which the concentrated aqueous feed stream comprises about 10 wt % to about 25 wt % total carbohydrates.

27. The process of claim 20 in which the concentrated aqueous feed stream comprises about 12 wt % to about 20 wt % total carbohydrates.

28. The process of claim 20 in which the concentrated aqueous feed stream comprises about 12 wt % to about 18 wt % total carbohydrates.

29. The process of claim 20 in which the concentrated aqueous feed stream comprises about 13 wt % to about 17 wt % total carbohydrates.

30. The process of claim 20 in which the organic solvent comprises a solvent selected from the group consisting of methyl acetate, ethyl acetate, iso-propyl acetate, n-propyl acetate, n-butyl acetate, amyl acetate, methyl ethyl ketone, methyl iso-butyl ketone, methyl iso-amyl ketone, methylene chloride, chloroform, n-butanol, and mixtures thereof.

31. A process according to claim 20, additionally comprising the steps of deacylation of the sucralose-6-ester to sucralose, and purifying and isolating the sucralose.

32. The process of claim 1 in which the first organic solvent comprises ethyl acetate.

33. The process of claim 1 in which the second organic solvent comprises ethyl acetate.

34. The process of claim 20 in which the organic solvent comprises ethyl acetate.

* * * * *

UNITED STATES PATENT AND TRADEMARK OFFICE
CERTIFICATE OF CORRECTION

PATENT NO. : 8,212,022 B2  
APPLICATION NO. : 12/416520  
DATED : July 3, 2012  
INVENTOR(S) : Edward Micinski and James Edwin Wiley, Jr.

It is certified that error appears in the above-identified patent and that said Letters Patent is hereby corrected as shown below:

At column 14, line 25, after the word "carbohydrate" and before the word "the" insert the word --in--

Signed and Sealed this
Twenty-sixth Day of February, 2013

Teresa Stanek Rea
*Acting Director of the United States Patent and Trademark Office*